(12) United States Patent
Lim

(10) Patent No.: US 10,280,746 B2
(45) Date of Patent: May 7, 2019

(54) CONCENTRIC CONTAINER FOR FLUID SAMPLING

(75) Inventor: Boon Buan Lim, Singapore (SG)

(73) Assignee: Halliburton Energy Services, Inc., Houston, TX (US)

( * ) Notice: Subject to any disclaimer, the term of this patent is extended or adjusted under 35 U.S.C. 154(b) by 372 days.

(21) Appl. No.: 14/422,218

(22) PCT Filed: Aug. 23, 2012

(86) PCT No.: PCT/US2012/051997
§ 371 (c)(1),
(2), (4) Date: Feb. 18, 2015

(87) PCT Pub. No.: WO2014/031118
PCT Pub. Date: Feb. 27, 2014

(65) Prior Publication Data
US 2015/0218942 A1    Aug. 6, 2015

(51) Int. Cl.
| | | |
|---|---|---|
| *G01F 1/00* | (2006.01) | |
| *G01N 1/10* | (2006.01) | |
| *G01N 1/18* | (2006.01) | |
| *G01N 1/20* | (2006.01) | |
| *E21B 49/08* | (2006.01) | |

(52) U.S. Cl.
CPC ............ *E21B 49/08* (2013.01); *E21B 49/081* (2013.01); *G01F 1/00* (2013.01); *G01N 1/18* (2013.01); *G01N 2001/1031* (2013.01); *G01N 2001/2071* (2013.01)

(58) Field of Classification Search
CPC .......... E21B 49/08; E21B 49/081; G01N 1/18
See application file for complete search history.

(56) References Cited

U.S. PATENT DOCUMENTS

| | | | |
|---|---|---|---|
| 6,688,390 B2 | 2/2004 | Bolze et al. | |
| 2003/0037929 A1* | 2/2003 | Leniek, Sr. | ............ E21B 43/127 166/369 |
| 2011/0139448 A1 | 6/2011 | Ciglenec | |
| 2011/0153225 A1* | 6/2011 | Mangal | ..................... G01F 1/00 702/24 |

FOREIGN PATENT DOCUMENTS

| | | | | |
|---|---|---|---|---|
| DE | 324662 C | * | 9/1920 | ................ F17C 1/04 |
| DE | 337400 C | | 5/1921 | |
| GB | 294943 A | | 11/1929 | |
| GB | 2398122 A | | 8/2004 | |

OTHER PUBLICATIONS

International Search Report and Written Opinion issued in related PCT Application No. PCT/US2012/051997 dated Jun. 25, 2013, 11 pages.
First Office Action issued by Mexican Patent Office in related Mexican Patent Application No. MX/a/2015/002334, dated Nov. 22, 2017, 6 pages.

* cited by examiner

*Primary Examiner* — Justin Seo
*Assistant Examiner* — John M Royston
(74) *Attorney, Agent, or Firm* — Benjamin Fite; Baker Botts L.L.P.

(57) ABSTRACT

Apparatus and methods for improved fluid sampling are disclosed. A sampling bottle for collection of a fluid sample comprises concentrically arranged first, second and third sampling containers (304A, 304B, 304C). First, second and third check valves (311, 312, 314) regulate flow of the sampling fluid from outside the sampling bottle into the first sampling container, and into the second and third sampling container.

16 Claims, 2 Drawing Sheets

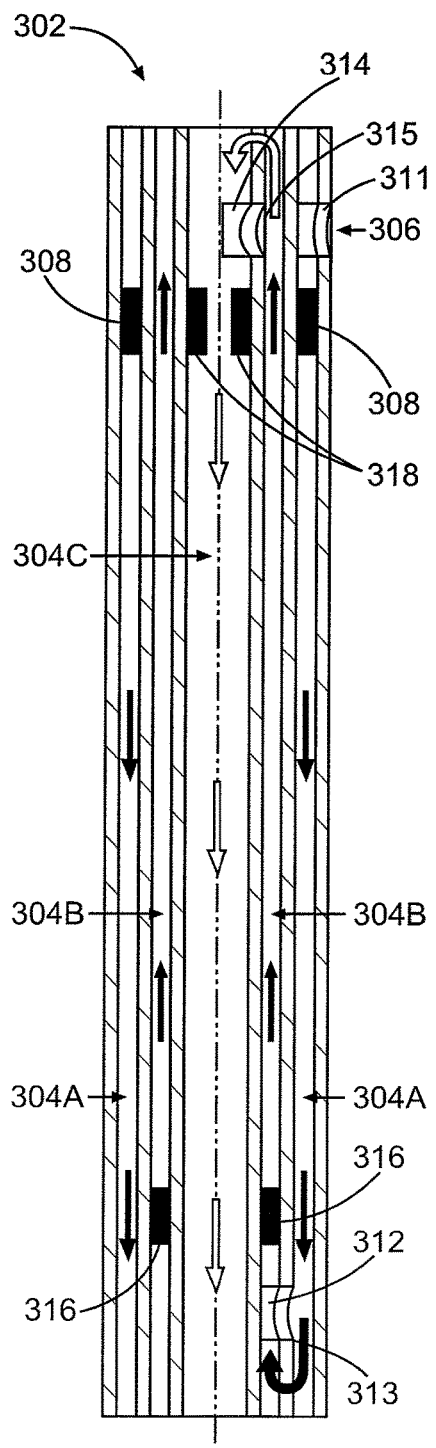
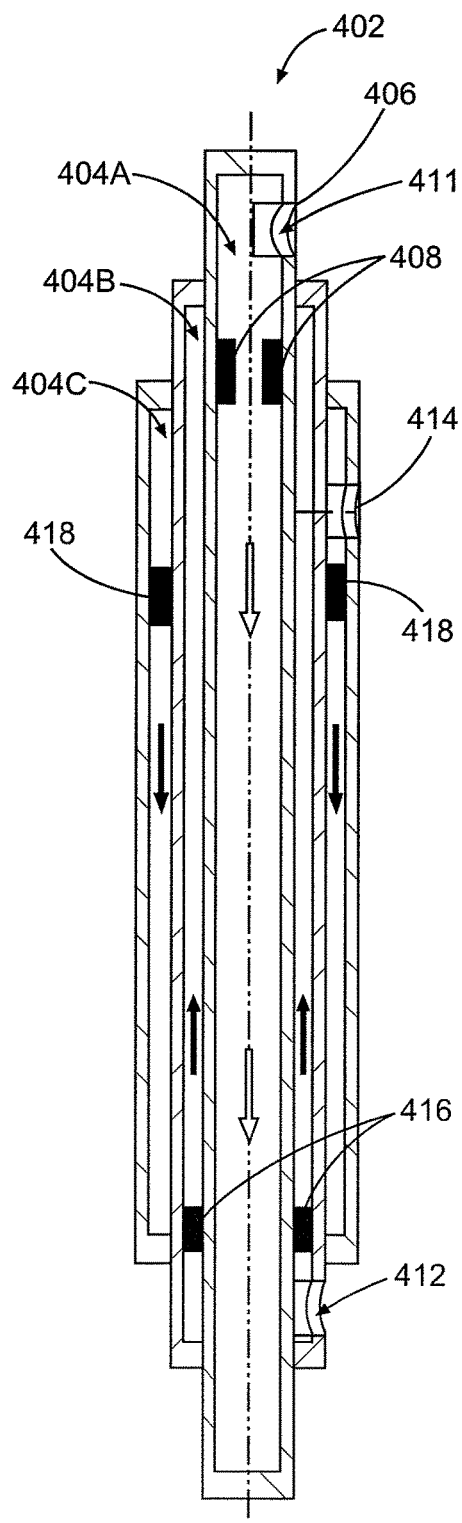
Fig. 2
Fig. 3

CONCENTRIC CONTAINER FOR FLUID SAMPLING

CROSS-REFERENCE TO RELATED APPLICATION

This application is a U.S. National Stage Application of International Application No. PCT/US2012/051997 filed Aug. 23, 2012, which is hereby incorporated by reference in its entirety.

BACKGROUND

The present invention relates generally to testing and evaluation of subterranean formation fluids and, more particularly, to apparatus and methods for improved fluid sampling.

When performing subterranean operations such as when drilling or completing wells, it is often desirable to perform tests on the formation penetrated by the wellbore. Such tests are typically performed in order to determine geological or other physical properties of the formation and fluids contained therein. For example, parameters such as permeability, porosity, fluid resistivity, temperature, pressure and saturation pressure may be determined by performing such tests. These and other characteristics of the formation and fluid contained therein may be determined by performing tests on the formation before the well is completed.

In order to evaluate prospects of an underground hydrocarbon reserve, a representative sample of formation fluids may be captured for detailed analysis. In a typical sampling procedure, a sample of the formation fluids may be obtained by lowering a sampling tool having one or more sampling containers into the wellbore on a conveyance such as a wireline, slick line, coiled tubing, jointed tubing or the like. When the sampling tool reaches the desired location in the wellbore, one or more ports may be opened to allow collection of the formation fluids. The desired location may be any axial location along the wellbore where it is desirable to obtain a fluid sample. The ports may be actuated in a variety of ways such as by electrical, hydraulic, or mechanical methods. Once the ports are opened, formation fluids travel through the ports and a sample of the formation fluids is collected within the sampling chamber of the sampling tool. After the sample has been collected, the sampling tool may be withdrawn from the wellbore so that the formation fluid sample may be analyzed.

Due to borehole size limits, typically sampling containers are used which have multiple long and slim containers arranged in a circular manner to optimize the number of samples that may be obtained downhole. However, this arrangement of sampling containers is prone to failure and poses significant engineering challenges. Specifically, because of their inherently fragile geometry, the containers are prone to sagging and bending at their middle section under the forces exerted thereon by the containers' own weight and/or other operations downhole. It is therefore desirable to develop a sampling container that can optimize storage capacity while being able to withstand the forces downhole.

Moreover, it may be desirable to incorporate one or more sensors into the sampling containers to facilitate monitoring of the sampling process from the surface. However, because existing sampling containers have a small diameter, they do not provide sufficient space to incorporate such sensor mechanisms.

BRIEF DESCRIPTION OF THE DRAWING(S)

The present disclosure will be more fully understood by reference to the following detailed description of the preferred embodiments of the present disclosure when read in conjunction with the accompanying drawings, in which like reference numbers refer to like parts throughout the views, wherein:

FIG. 2 depicts a cross-sectional view of arrangement of sampling containers in accordance with a first embodiment of the present disclosure; and FIG. 3 depicts a cross-sectional view of arrangement of sampling containers in accordance with a second embodiment of the present disclosure.

Figure 1:
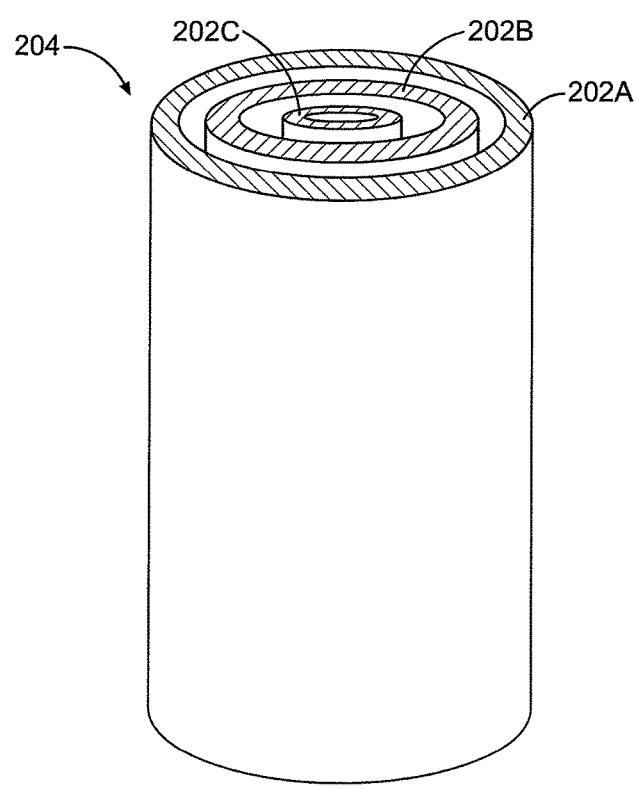
FIG. 1 depicts an arrangement of sampling containers in accordance with an embodiment of the present disclosure.

The disclosure may be embodied in other specific fauns without departing from the spirit or essential characteristics thereof. The present embodiments are therefore to be considered in all respects as illustrative and not restrictive, the scope of the disclosure being indicated by the appended claims rather than by the foregoing description, and all changes which come within the meaning and range of equivalency of the claims are therefore intended to be embraced therein.

DETAILED DESCRIPTION OF THE DISCLOSURE

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components.

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such as wires, optical fibers, microwaves, radio waves, and other electromagnetic and/or optical carriers; and/or any combination of the foregoing. The terms "couple" or "couples" as used herein are intended to mean either an indirect or direct connection. Thus, if a first device couples to a second device, that connection may be through a direct connection, or through an indirect mechanical or electrical connection via other devices and connections. Similarly, the term "communicatively coupled" as used herein is intended to mean either a direct or an indirect communication connection. Such connection may be a wired or wireless connection such as, for example, Ethernet or LAN. Such wired and wireless connections are well known to those of ordinary skill in the art and will therefore not be discussed in detail herein. Thus, if a first device communicatively couples to a second device, that connection may be through a direct connection, or through an indirect communication connection via other devices and connections. Finally, the term "fluidically coupled" as used herein is intended to mean that there is either a direct or an indirect fluid flow path between two components.

The present invention relates generally to testing and evaluation of subterranean formation fluids and, more particularly, to apparatus and methods for improved fluid sampling.

FIG. 1 depicts an arrangement of sampling containers 202A, 202B, 202C in accordance with an embodiment of the present disclosure. As discussed above, the sampling containers 202A-C may be part of a sampling tool. Specifically, the sampling containers 202A, 202B, 202C may be placed in a concentric arrangement, together forming a multi-compartment sampling bottle 204. The sampling containers 202A-202C may be placed in this concentric arrangement using a number of different methods. For instance, in one embodiment, the sampling containers 202A-C may have studs or standoffs in between each layer. In other embodiments, the sampling containers 202A-C may be solidly welded together at the base of the sampling container or at another point along the length of the sampling containers. This concentric arrangement permits using a sampling container with a larger cylindrical diameter which will significantly improve the bending resistance of the sampling container and provide a better protection to any components that may be located therein.

Different fluid samples may be stored in distinct sampling containers 202A-C of the sampling bottle 204. A number of different mechanisms may be utilized to keep the contents of the different sampling containers 202A-C separated. For instance, a one-way valve, a cap, a seal, a combination thereof, or any other separation device may be used at the distal ends of the concentric sampling containers 202A-C to keep the contents separated.

Moreover, the increase in the size of the sampling containers 202A-C relative to prior art sampling containers permits installation of a feedback system in the sampling container to monitor the sampling process. Specifically, in one embodiment, one or more sensors may be placed inside one or more of the sampling containers 202A-C. The sensor may be any desirable sensor including, but not limited to, a pressure sensor or a flow rate sensor. The sensor may be used to monitor the flow of the fluid sample into the sampling containers 202A-C and determine when a sufficient amount of the fluid sample has been stored therein. In one embodiment, the sensors may be communicatively coupled to an information handling system. The information handling system may include a computer-readable medium. A threshold value for the amount of the fluid sample needed may then be stored in the computer readable medium. The sensors in the containers 202A-C may communicate the amount of fluid sample collected therein to the information handling system. The information handling system may then compare the amount of fluid collected and once the amount collected is equal to or exceeds the threshold value the collection process may be terminated. Accordingly, the feedback system may be used to determine whether the sampling containers 202A-C have been successfully filled without having to remove the sampling tool to the surface for a visual inspection.

As would be appreciated by those of ordinary skill in the art, although the sampling bottle 204 is shown as having three containers 202A, 202B and 202C for illustrative purposes only, in other embodiments more or fewer containers may be used in the sampling bottle 204.

FIGS. 2 and 3 depict obtaining fluid samples using an improved sampling bottle in accordance with certain embodiments of the present disclosure. Turning to FIG. 2, a sampling bottle 302 is provided which includes three concentric sampling containers 304A, 304B, 304C. The sampling bottle 302 may include a sample inlet 306 that may be operable to direct a fluid sample into any of the containers 304A, 304B, 304C of the sampling bottle 302. A flow meter 308 may be positioned in the sampling container 304A proximate to the sample inlet 306. The flow meter 308 detects fluid flow into the sampling container 304A. In one embodiment, the flow meter 308 may provide a notification to the user once the fluid sample begins to flow into the sampling bottle 302 through the sample inlet 306. Additionally, a second flow meter 316 may be positioned in the second container 304B and a third flow meter 318 may be placed in the third container 304C, with each flow meter being used to monitor fluid flow into the respective container. A first one-way check valve 311 may be used to control or regulate fluid flow into the sampling bottle 302 through the sample inlet 306. A second one-way check valve 312 is placed at an inlet 313 between the first container 304A and the second container 304B, regulating fluid flow through the inlet 313, and a third one-way check valve 314 is placed at an inlet 315 between the second container 304B and the third container 304C, regulating fluid flow through the inlet 315. Regulation of fluid flow by the one-way check valves 311, 312, 314 may include preventing fluid flow by closing a corresponding inlet. In accordance with certain embodiments, multiple samples may be obtained at the same axial location in a wellbore using the sampling bottle 302.

In certain embodiments, the containers 304A-C are depressurized to substantially create vacuum therein before performing sampling operations. In operation, a first fluid sample may flow through the sample inlet 306 into the first container 304A. The first one-way check valve 311 may regulate fluid flow through the sample inlet 306 into the first container 304A. As the first fluid sample flows into the first container 304A, pressure inside the first container 304A builds up and eventually the inner pressure of the first container 304A and the outer pressure reach an equilibrium. Accordingly, when a sufficient amount of the first fluid sample has been collected in the first container 304A and the pressure build up resulting from the accumulation of the first fluid sample in the first container 304A is large enough, the pressure will overcome the second one-way check valve 312, opening it.

The second one-way check valve 312 regulates fluid flow into the second container 304B through the inlet 313. Accordingly, once the second one-way check valve 312 opens, the first fluid sample will flow into the second container 304B from the first container 304A. As the first fluid sample flows into the second container 304B from the first container 304A, negative pressure will be created at the first container 304A and cause a new fluid sample from formation to fill up the first container 304A. Once, the first and second containers 304A, 304B reach similar pressure as the wellbore, the third one-way check valve 314 is triggered to open and allow the second sample to flow into the third container 304C. The newly collected sample at the first container 304A will be pulled into the second container 304B due to the newly negative pressure created by the third container 304C. While sample fluid from the first container 304A flows into the second container 304B, another negative pressure is formed at the first container 304A. Consequently, a new fluid sample may be collected at the first container 304A from the formation. The three one-way check valves may be programmed to close once they reach a predetermined pressure level to prevent further fluid flow into the corresponding container. Specifically, once the pressure inside the third container 304C resulting from containment of a fluid sample reaches a predetermined amount, the third one-way check valve 314 prevents further addition of a fluid to the third container 304C. The collection of a fluid sample in the first container 304A and the second container 304B may be regulated in the same manner.

In certain embodiments, the one-way check valves 311, 312, 314 may be selectively opened and closed to collect a desired amount of sampling fluids therein. Specifically, the amount of sampling fluid collected in each sampling container 304A-C does not have to be dependent upon the fluid pressure build up in each container and may instead be regulated by opening and closing the one-way check valves 311, 312, 314 based on the feedback of the flowmeters 308, 316, and 318. As a result, any desired amount of fluid sample may be collected in each container 304A-C.

As would be appreciated by those of ordinary skill in the art, although the sampling bottle 302 is shown as having three containers 304A, 304B and 304C for illustrative purposes only, in other embodiments more or fewer containers may be used in the sampling bottle 302 in the same manner.

FIG. 3 depicts a sampling bottle 402 in accordance with certain embodiments of the present disclosure which may be used to obtain multiple samples at different locations along the wellbore. The sampling bottle 402 includes three concentric containers 404A, 404B, 404C. The first container 404A includes a first sample inlet 406 having a one-way check valve 411 to control the flow of a fluid sample into the sampling container 404A. Similarly, a second one-way check valve 412 controls fluid sample flow into the second container 404B and a third one-way check valve 414 controls fluid sample flow into the third container 404C. The one-way check valves 411, 412, 414 may have different pressure ratings thereby facilitating fluid collection at different depths or locations in the wellbore having different downhole pressures. Accordingly, the fluid sample from each particular depth will be collected in a separate container in the sampling bottle 402. Additionally, as with the embodiment of FIG. 2, a first flow meter 408 may be used to monitor fluid flow into the first container 404A, a second flow meter 416 may be used to monitor fluid flow into the second container 404B and a third flow meter 418 may be used to monitor fluid flow into the third container 404C. As would be appreciated by those of ordinary skill in the art, although the sampling bottle 402 is shown as having three concentric containers 404A, 404B and 404C for illustrative purposes only, in other embodiments more or fewer containers may be used in the sampling bottle 402 in the same manner.

In certain embodiments, the flow meters discussed in conjunction with FIGS. 2 and 3 may be communicatively coupled to an information handling system (not shown). The information handling system may include a user interface allowing a user to monitor the amount of fluid collected in each of the sampling containers to ensure the desired amount is collected before removing the sampling bottle or changing its location. Moreover, in certain embodiments, the check valves discussed in conjunction with FIGS. 2 and 3 may be communicatively coupled to the information handling system allowing a user to open and close each check valve as desired. Accordingly, the user may control when and how much of a fluid sample is collected in each of the sampling containers by selectively opening and closing the check valves.

The improved designs of the sampling bottle is less prone to damage. Specifically, if the sampling bottle is simply supported, its peak moment (M) under a uniformly distributed load may be defined as:

$$M = \frac{PL^2}{8} \quad [\text{Eq. 1}]$$

where P is the applied force and L is the length. Accordingly, the stress ($\sigma$) on the sampling bottle may be determined as:

$$\sigma = \frac{My}{I} \quad [\text{Eq. 2}]$$

where M is the peak moment, y is the distance from the center axis and I is the area moment of inertia. Further, the area moment of inertia (I) for a hollow tube may be determined as:

$$I = \frac{\pi}{64}(OD^4 - ID^4) \quad [\text{Eq. 3}]$$

where OD is the outer diameter of the hollow tube and ID is the inner diameter of the hollow tube. Equations 1-3 may be used to obtain an expression for the stress ($\sigma$) applied to the hollow tube:

$$\sigma = \frac{4}{\pi} * \frac{P*OD*L^2}{(OD^4 - ID^4)} \quad [\text{Eq. 4}]$$

Accordingly, the applicable stress to the prior art sampling containers of ($\sigma 1A$, $\sigma 1B$) may be compared to the applicable stress to the concentric sampling container of the present disclosure ($\sigma new$) as follows:

$$\sigma 1A : \sigma 1B : \sigma new = \frac{OD1A}{(OD1A^4 - ID1A^4)} : \frac{ID1B}{(OD1B^4 - ID1B^4)} : \frac{ODnew}{(ODnew^4 - IDnew^4)} \quad [\text{Eq. 5}]$$

As a result, as shown in more detail in the example below, the increase in the diameter of the sampling containers significantly improves the ability of the containers to withstand the stress.

Accordingly, the concentric configuration of the sampling containers as disclosed herein improves the structural integrity of the sampling tool, making tool handling easier. Additionally, the proposed improvements simplify the monitoring of the sampling process. As a result, the proposed improvements cut down tool downtime and enhance the performance of the sampling process.

As would be appreciated by those of ordinary skill in the art, with the benefit of this disclosure, the sampling bottle of FIGS. 1, 2, and 3 is shown as having three containers for illustrative purposes only. Accordingly, in other embodiments, more or fewer containers may be used in the sampling bottle in the same manner without departing from the scope of the present disclosure.

EXAMPLE

In one example, where the borehole diameter was limited to 2.05", the maximum bottle OD for a sampling bottle having three sampling containers or a sampling bottle having seven sampling containers in accordance with the prior art and the improved concentric design of FIG. 1 were 1.025", 0.683" and 2.05", respectively. Accordingly, with all containers having the same wall thickness, the stress ratio for the three different implementations using Eq. 5 would be:

$$\sigma 1A : \sigma 1B : \sigma 1new = 4.29 : 10.39 : 1$$

Accordingly, the improved concentric sampling container of the present disclosure can withstand a stress loading that is approximately four times larger than that of the configuration of a prior art sampling bottle having three sampling containers and approximately ten times larger than that of the configuration of a prior art sampling bottle having seven sampling containers.

Moreover, in addition to being able to withstand a higher stress load, the new configuration maximizes the usable area of the borehole cross section compared to the wastage of approximately 25% of the usable space in implementation of a prior art sampling bottle having three sampling containers and 22.2% in the implementation of a prior art sampling bottle having seven sampling containers. This increase in the available usable space facilitates the implementation of a feedback system as discussed above.

Therefore, the present disclosure is well adapted to carry out the objects and attain the ends and advantages mentioned as well as those which are inherent therein. While the disclosure has been depicted and described by reference to exemplary embodiments of the disclosure, such a reference does not imply a limitation on the disclosure, and no such limitation is to be inferred. The disclosure is capable of considerable modification, alteration, and equivalents in form and function, as will occur to those ordinarily skilled in the pertinent arts and having the benefit of this disclosure. The depicted and described embodiments of the disclosure are exemplary only, and are not exhaustive of the scope of the disclosure. Consequently, the disclosure is intended to be limited only by the spirit and scope of the appended claims, giving full cognizance to equivalents in all respects. The terms in the claims have their plain, ordinary meaning unless otherwise explicitly and clearly defined by the patentee.

What is claimed is:

1. A sampling bottle for collection of a fluid sample comprising:
    a first sampling container, wherein the first sampling container comprises a first inlet that receives a first fluid sample;
    a second sampling container located within the first sampling container;
    a first check valve allowing flow of the first fluid sample from outside the sampling bottle into the first inlet of the first sampling container; and
    a second check valve at a second inlet between the first sampling container and the second sampling container allowing flow of a second fluid sample from the first inlet of the first sampling container into the second inlet of the second sampling container.

2. The sampling bottle of claim 1, wherein the second sampling container is concentrically located within the first sampling container.

3. The sampling bottle of claim 1, further comprising a first flow meter, wherein the first flow meter monitors flow of the first fluid sample into the first sampling container.

4. The sampling bottle of claim 3, wherein the first flow meter is communicatively coupled to an information handling system and wherein the first flow meter communicates amount of fluid flow into the first sampling container to the information handling system.

5. The sampling bottle of claim 3, further comprising a second flow meter, wherein the second flow meter monitors flow of the second fluid sample into the second container.

6. The sampling bottle of claim 1, wherein an information handling system is operable to selectively open and close at least one of the first check valve and the second check valve.

7. The sampling bottle of claim 1, further comprising a third sampling container located within the second sampling container.

8. A method of collecting fluid samples comprising:
    placing a sampling bottle at a desired location in a wellbore,
    wherein the sampling bottle comprises a first sampling container having a first check valve and a second sampling container having a second check valve,
    wherein the second sampling container is located within the first sampling container; and
    collecting a first fluid sample in the first sampling container and collecting a second fluid sample in the second sampling container,
    wherein collecting the first fluid sample and the second fluid sample comprises selectively opening and closing the first check valve to allow flow of the first fluid sample from outside the sampling bottle into the first sampling container and the second check valve to allow flow of the second fluid sample from the first sampling container into the second sampling container.

9. The method of claim 8, wherein the second sampling container is concentrically located within the first sampling container.

10. The method of claim 8, wherein the sampling bottle further comprises a first flow meter, wherein the first flow meter monitors flow of the first fluid sample into the first container.

11. The method of claim 10, wherein the first flow meter is communicatively coupled to an information handling system and wherein the first flow meter communicates amount of fluid flow into the first sampling container to the information handling system.

12. The method of claim 10, wherein the sampling bottle further comprises a second flow meter, wherein the second flow meter monitors flow of the second fluid sample into the second sampling container.

13. The method of claim 8, further comprising communicatively coupling an information handling system to the sampling bottle, wherein the information handling system is operable to selectively open and close at least one of the first check valve and the second check valve.

14. The method of claim 8, wherein the sampling bottle further comprises a third sampling container located within the second sampling container.

15. A sampling bottle comprising:
a plurality of concentric sampling containers;
a plurality of check valves,
wherein at least one of the plurality of check valves allows flow of a sampling fluid from outside the sampling bottle into an outermost one of the at least one of the plurality of check valves, wherein the outermost one of the at least one of the plurality of check valves is at a first inlet of a first one of the plurality of concentric sampling containers, and
wherein at least one or more of the plurality of check valves at a second inlet between the first one of the plurality of concentric sampling containers and a second one of the plurality of concentric sampling containers allows flow of the sampling fluid from the first inlet of the first one of the plurality of concentric sampling containers into the second inlet of the second one of the plurality of concentric sampling containers; and
a flow meter corresponding to at least one of the plurality of concentric sampling containers, wherein the flow meter monitors amount of fluid directed into the at least one of the plurality of concentric sampling containers.

16. The sampling bottle of claim 15, further comprising an information handling system communicatively coupled to the sampling bottle, wherein the information handling system is operable to at least one of control operation of the at least one of the plurality of check valves and monitor the flow meter.

* * * * *